United States Patent
Nahum et al.

(10) Patent No.: US 12,220,182 B2
(45) Date of Patent: Feb. 11, 2025

(54) NAVIGATION METHOD FOR POSITIONING A MEDICAL ROBOT

(71) Applicant: Quantum Surgical, Montpellier (FR)

(72) Inventors: Bertin Nahum, Castelnau-le-Lez (FR); Fernand Badano, Lyons (FR); Lucien Blondel, Montpellier (FR)

(73) Assignee: QUANTUM SURGICAL, Montpellier (FR)

( * ) Notice: Subject to any disclaimer, the term of this patent is extended or adjusted under 35 U.S.C. 154(b) by 348 days.

(21) Appl. No.: 17/756,172

(22) PCT Filed: Nov. 17, 2020

(86) PCT No.: PCT/FR2020/052100
§ 371 (c)(1),
(2) Date: May 18, 2022

(87) PCT Pub. No.: WO2021/099729
PCT Pub. Date: May 27, 2021

(65) Prior Publication Data
US 2022/0409288 A1    Dec. 29, 2022

(30) Foreign Application Priority Data
Nov. 19, 2019  (FR) ...................... 1912907

(51) Int. Cl.
*A61B 34/20*    (2016.01)
*A61B 34/30*    (2016.01)
(Continued)

(52) U.S. Cl.
CPC .............. *A61B 34/20* (2016.02); *A61B 34/30* (2016.02); *A61B 90/39* (2016.02); *G06T 7/73* (2017.01);
(Continued)

(58) Field of Classification Search
CPC . A61B 34/20; A61B 34/2055; A61B 34/2059; A61B 34/2057; A61B 34/2065; A61B 2090/3618
See application file for complete search history.

(56) References Cited

U.S. PATENT DOCUMENTS

2008/0285725 A1* 11/2008 Dehler .................. A61B 6/583
378/207
2015/0302590 A1* 10/2015 Hong ....................... G06T 7/74
348/46
(Continued)

FOREIGN PATENT DOCUMENTS

CN    102866433 A    1/2013
CN    103491871 A    1/2014
(Continued)

OTHER PUBLICATIONS

International Search Report and Written Opinion mailed, Jan. 15, 2021, issued for PCT/FR2020/052100.

*Primary Examiner* — Benjamin O Dulaney
(74) *Attorney, Agent, or Firm* — ArentFox Schiff LLP

(57) ABSTRACT

The invention relates to an optical navigation system for determining the position of a patient's anatomy of interest. The system comprises a locating device having at least two optical sensors and a patient reference having at least three optical markers. The system also comprises a reflecting device. When the line of sight between the patient reference and an optical sensor is intersected by an obstacle, the optical sensors are configured to measure, for each optical marker of the patient reference, a quantity representing the position of said optical marker in the frame of reference of the locating device from optical radiation originating from said optical marker and having a path reflected by the reflecting device to each optical sensor.

19 Claims, 8 Drawing Sheets

Figure 1:
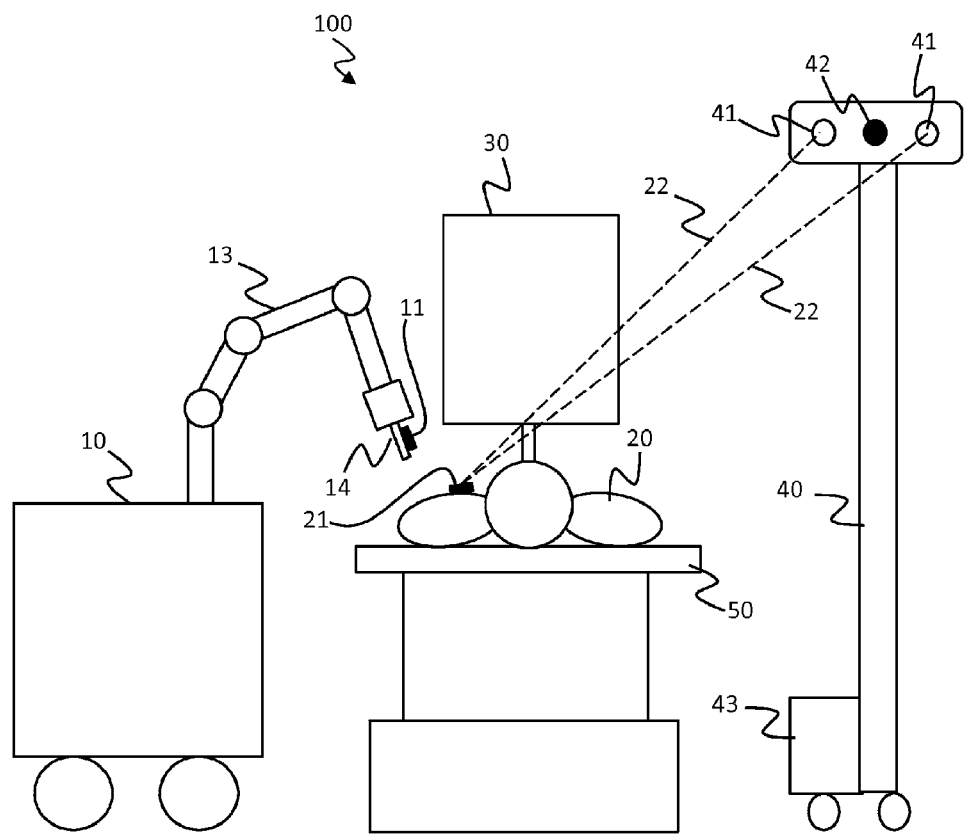

(51) Int. Cl.
*A61B 90/00* (2016.01)
*G06T 7/73* (2017.01)

(52) U.S. Cl.
CPC ............. *A61B 2034/2055* (2016.02); *A61B 2034/2059* (2016.02); *A61B 2090/3618* (2016.02); *A61B 2090/3966* (2016.02); *A61B 2090/3979* (2016.02); *A61B 2090/3983* (2016.02)

(56) References Cited

U.S. PATENT DOCUMENTS

| | | | |
|---|---|---|---|
| 2016/0035108 A1* | 2/2016 | Yu | A61B 5/721 382/131 |
| 2016/0142683 A1* | 5/2016 | Seesselberg | H04N 7/183 348/143 |
| 2019/0038362 A1 | 2/2019 | Nash et al. | |
| 2019/0199915 A1 | 6/2019 | Coiseur | |
| 2019/0321657 A1* | 10/2019 | Hale | A61N 5/1075 |
| 2024/0245469 A1* | 7/2024 | Row | A61B 34/20 |

FOREIGN PATENT DOCUMENTS

| | | |
|---|---|---|
| CN | 105916462 A | 8/2016 |
| CN | 106802658 A | 6/2017 |
| CN | 106999247 A | 8/2017 |
| CN | 108024693 A | 5/2018 |
| CN | 108186117 A | 6/2018 |
| CN | 109464196 A | 3/2019 |
| CN | 109938809 A | 6/2019 |
| CN | 109952070 A | 6/2019 |
| CN | 110051436 A | 7/2019 |
| EP | 2944285 A1 | 11/2015 |
| EP | 3501443 A1 | 6/2019 |
| WO | 2016014718 A1 | 1/2016 |

\* cited by examiner

NAVIGATION METHOD FOR POSITIONING A MEDICAL ROBOT

CROSS-REFERENCE TO RELATED APPLICATIONS

This application is a National Phase of PCT/FR2020/052100, filed on Nov. 17, 2020, which claims priority to FR1912907, filed on Nov. 19, 2019, the disclosures of which are hereby incorporated by reference in their entireties.

FIELD OF THE INVENTION

The present invention belongs to the field of minimally invasive and non-invasive medical interventions assisted by a medical robot. The invention relates in particular to an optical navigation system for determining the position of an anatomy of interest of a patient in order to optimally position a medical instrument attached to one end of an articulated arm of the medical robot. In particular, the invention makes it possible to determine the position of the anatomy of interest even when an obstacle prevents obtaining a direct line of sight between an optical marker, situated at the anatomy of interest, and an optical sensor of the navigation system. The invention also relates to a method for determining the position of an anatomy of interest of a patient.

PRIOR ART

Many medical interventions, such as minimally invasive or non-invasive medical interventions, require very precise positioning or movement of a medical instrument (for example a needle, a catheter, an electrode, an ultrasound generator, a drill bit, etc.) with respect to an anatomy of interest of a patient (for example the liver, lungs, kidneys, vertebrae, etc.). The practitioner who performs this type of medical intervention can be assisted by a medical robot. In this case, the medical robot positions, maintains and/or guides a medical instrument with respect to an anatomy of interest of a patient by virtue of a navigation system. The medical instrument is attached, for example, to one end of an articulated arm of the medical robot. The navigation system makes it possible to determine the position of the medical instrument and the position of the anatomy of interest. The information concerning the respective positions of the medical instrument and of the anatomy of interest relative to each other then allows the medical robot to configure its articulated arm in such a way that the medical instrument is positioned optimally with respect to the anatomy of interest.

There are different types of navigation systems. Electromagnetic navigation systems have the disadvantage of being sensitive to interference and distortion of the electromagnetic field in the presence of metallic materials (such as the motors of a medical robot). Optical navigation systems for their part have the disadvantage of no longer functioning when the line of sight between a marker, positioned at the anatomy of interest, and an optical sensor of the navigation system is cut by an obstacle (this is the case, for example, when the practitioner comes between said marker and said optical sensor).

It is generally not sufficient to determine the position of the anatomy of interest at a favorable moment when a direct line of sight is available, since the anatomy of interest of the patient may be in motion, for example on account of the breathing movements of the patient or on account of the displacement of the anatomy by the practitioner. It is therefore necessary to be able to follow the position of the anatomy of interest over the course of time with the aid of the navigation system, even during periods when the line of sight between a marker, positioned at the anatomy of interest, and an optical sensor of the navigation system is cut by an obstacle.

Several solutions of the prior art consist in optimizing the positioning of the markers and of the optical sensors used, in order to reduce the risk of the line of sight being cut by an obstacle. These solutions are generally complex and do not always make it possible to guarantee the operation of the optical navigation system when the line of sight is cut by an obstacle.

The patent application EP 3501443 A1 discloses in particular a system comprising a rotating component integrated in a scialytic lamp in order to move a camera to a position suitable for targeting an anatomy of interest of a patient when an obstacle prevents obtaining a direct line of sight.

Some solutions of the prior art seek to combine an optical navigation system with another complementary navigation system (for example an electromagnetic navigation system) which would make it possible to guarantee the operation of the navigation system when the line of sight is cut by a obstacle. However, these solutions result in complex and expensive systems, the accuracy of which may be affected by the presence of metallic objects.

DISCLOSURE OF THE INVENTION

The aim of the present invention is to overcome all or some of the disadvantages of the prior art, in particular those set out above.

To this end, and according to a first aspect, the present invention provides an optical navigation system for determining the position of an anatomy of interest of a patient. The system comprises in particular a patient reference, intended to be positioned on the patient at the anatomy of interest, a locating device, and a control unit. The locating device has at least two optical sensors. The patient reference has at least three optical markers. The respective positions of the optical markers of the patient reference relative to each other are known a priori by the control unit. The optical navigation system moreover has a reflecting device, the position of which in a frame of reference of the locating device can be determined by the control unit. When a direct line of sight between the patient reference and each optical sensor is available, the optical sensors are configured to measure, for each optical marker of the patient reference, a parameter representative of the position of said optical marker in the frame of reference of the locating device, on the basis of optical radiation coming from said optical marker and having for each optical sensor a direct path between said optical marker and said optical sensor. When a direct line of sight between the patient reference and an optical sensor is cut by an obstacle, the optical sensors are configured to measure, for each optical marker of the patient reference, a parameter representative of the position of said optical marker in the frame of reference of the locating device, on the basis of optical radiation coming from said optical marker and having a path reflected by the reflecting device toward each optical sensor. The control unit is configured to determine, from the measurements carried out by the optical sensors, the position of the patient reference in the frame of reference of the locating device, and to deduce therefrom the position of the anatomy of interest in said frame of reference.

In the present application, "optical radiation" is understood to mean electromagnetic radiation within a wavelength range from 100 nm (one hundred nanometers) to 1 mm (one millimeter). Thus, infrared radiation, visible light radiation and ultraviolet radiation are optical radiation. The term "optical ray" is sometimes used to define a particular path taken by optical radiation.

In the present application, the term "position" represents the position and orientation in the three dimensions of a spatial frame of reference.

The expression "the position of the reflecting device can be determined by the control unit" means that the position of the reflecting device is known a priori by the control unit (for example, the position of the reflecting device is saved in a memory of the control unit), or else that it can be determined by the control unit (for example with the aid of optical markers arranged on the reflecting device).

With such arrangements, the optical navigation system according to the invention is able to determine the position of the anatomy of interest of the patient even when the line of sight is cut by an obstacle (for example by a practitioner who will have to perform a medical intervention on the anatomy of interest, or by the medical robot that assists said practitioner).

In particular embodiments, the invention can moreover include one or more of the following features, taken in isolation or in all of the technically possible combinations.

In particular embodiments, the reflecting device has at least three optical markers. The respective positions of the optical markers of the reflecting device relative to each other are known a priori by the control unit.

In particular embodiments, during a period when a direct line of sight between the patient reference and each optical sensor is available, the control unit is configured to estimate a movement followed by the patient reference in the frame of reference of the locating device during a breathing cycle of the patient. Then, at a time when a direct line of sight between the patient reference and an optical sensor is no longer available, the control unit is configured to determine the position of the patient reference as a function, on the one hand of the measurements carried out by the optical sensors on the basis of the optical radiation coming from the optical markers of the patient reference and reflected by the reflecting device, and as a function, on the other hand, of the estimated movement of the patient reference.

In particular embodiments, the patient reference moreover has at least three radiopaque markers. The respective positions of the radiopaque markers relative to each other are known a priori by the control unit.

In particular embodiments, the position of the anatomy of interest in the frame of reference of the locating device is determined as a function of the position of the patient reference in said frame of reference and as a function of a medical image of the anatomy of interest of the patient on which the radiopaque markers of the patient reference are visible.

In particular embodiments, the position of the anatomy of interest in the frame of reference of the locating device is moreover determined as a function of a biomechanical model of the anatomy of interest.

In particular embodiments, the optical navigation system has three orthogonal reflecting devices in pairs.

In particular embodiments, the optical navigation system moreover has a robot reference intended to be positioned at a distal end of an articulated arm of a medical robot. The robot reference has at least three optical markers. The respective positions of the optical markers relative to each other are known a priori by the control unit. When a direct line of sight between the robot reference and each optical sensor is available, the optical sensors of the locating device are configured to measure, for each optical marker of the robot reference, a parameter representative of the position of said optical marker in the frame of reference of the locating device, on the basis of optical radiation coming from said optical marker and having for each optical sensor a direct path between said optical marker and said optical sensor. When a direct line of sight between the robot reference and an optical sensor is cut by an obstacle, the optical sensors are configured to measure, for each optical marker of the robot reference, a parameter representative of the position of said optical marker in the frame of reference of the locating device, on the basis of optical radiation coming from said optical marker and having a path reflected by the reflecting device toward each optical sensor. The control unit is configured to determine the position of the robot reference in the frame of reference of the locating device from the measurements thus carried out by the optical sensors.

In particular embodiments, the optical navigation system moreover has a medical robot comprising an articulated arm. The robot reference is positioned at a distal end of the articulated arm. The medical robot moreover has articulation coders of the articulated arm, making it possible to determine at any time the position of the robot reference in a frame of reference of the medical robot. The medical robot is configured to transmit to the control unit the position of the robot reference in the frame of reference of the robot. The control unit is configured to deduce therefrom the position of a medical instrument, attached to the distal end of the articulated arm of the medical robot, with respect to the anatomy of interest of the patient.

In particular embodiments, the optical markers of the patient reference and/or of the robot reference are active markers, and the optical radiation coming from an optical marker is infrared radiation generated by said optical marker.

In particular embodiments, the optical markers of the patient reference and/or of the robot reference are passive markers, and the optical radiation coming from an optical marker is infrared radiation generated by the locating device and reflected by said optical marker.

According to a second aspect, the present invention relates to a method for determining the position of an anatomy of interest of a patient during a surgical intervention. The method is implemented by an optical navigation system which comprises a patient reference, intended to be positioned on the patient at the anatomy of interest, and also a locating device. The respective positions of the optical markers relative to each other are known a priori. The locating device has at least two optical sensors. The patient reference has at least three optical markers. The optical navigation system moreover has a reflecting device whose position in a frame of reference of the locating device is known. The method has the following steps:

when a direct line of sight between the patient reference and each optical sensor is available, a measurement, for each optical marker of the patient reference, of a parameter representative of the position of said optical marker in the frame of reference of the locating device, on the basis of optical radiation coming from said optical marker and having for each optical sensor a direct path between said optical marker and said optical sensor, when a direct line of sight between the patient reference and an optical sensor is cut by an obstacle, a measurement, for each optical marker of the patient reference, of a parameter representative of the position of said optical marker in the frame of reference of the locating device, on the basis of optical radiation coming from said optical marker and having a path reflected by the reflecting device toward each optical sensor, a determination, from the measurements thus carried out by the optical sensors, of the position of the patient reference in the frame of reference of the locating device, a determination, in said frame of reference of the locating device, of the position of the anatomy of interest on the basis of the position of the patient reference.

It should be noted that the position of the anatomy of interest of the patient and the positioning of the medical instrument attached to one end of an articulated arm of the medical robot take place prior to the execution of the medical maneuver by the practitioner. Thus, the method according to the invention for determining the position of an anatomy of interest of a patient does not include a step of treatment by therapy or surgery.

In particular embodiments, the invention can moreover comprise one or more of the following features, taken in isolation or in all technically possible combinations.

In particular embodiments, the method moreover has the following steps:

during a period when a direct line of sight between the patient reference and each optical sensor is available, an estimation of a movement followed by the patient reference in the frame of reference of the locating device during a breathing cycle of the patient, at a time when a direct line of sight between the patient reference and an optical sensor is no longer available, a determination of the position of the patient reference as a function, on the one hand, of the measurements carried out by the optical sensors, on the basis of the optical radiation coming from the optical markers of the patient reference and reflected by the reflecting device, and as a function, on the other hand of the estimated movement of the patient reference.

In particular embodiments, the determination of the position of the anatomy of interest in the frame of reference of the locating device is moreover carried out on the basis of a medical image of the anatomy of interest of the patient on which radiopaque markers of the patient reference are visible.

In particular embodiments, the determination of the position of the anatomy of interest in the frame of reference of the locating device is moreover carried out on the basis of a biomechanical model of the anatomy of interest.

In particular embodiments, the optical navigation system moreover has a robot reference intended to be positioned at a distal end of an articulated arm of a medical robot. The robot reference has at least three optical markers, the respective positions of the optical markers relative to each other being known a priori. The method moreover has the following steps:

when a direct line of sight between the robot reference and each optical sensor is available, a measurement, for each optical marker of the robot reference, of a parameter representative of the position of said optical marker in the frame of reference of the locating device, on the basis of optical radiation coming from said optical marker and having for each optical sensor a direct path between said optical marker and said optical sensor, when a direct line of sight between the robot reference and an optical sensor is cut by an obstacle, a measurement, for each optical marker of the robot reference, of a parameter representative of the position of said optical marker in the frame of reference of the locating device, on the basis of optical radiation coming from said optical marker and having a path reflected by the reflecting device toward each optical sensor, a determination of the position of the robot reference in the frame of reference of the locating device, on the basis of the measurements thus carried out by the optical sensors.

In particular embodiments, the optical navigation system moreover has a medical robot. The medical robot has an articulated arm, at a distal end of which the robot reference is positioned. The medical robot also has articulation coders of the articulated arm, making it possible to determine at any time the position of the robot reference in a frame of reference of the medical robot. The method then includes a step of determining the position of a medical instrument, attached to the distal end of the articulated arm of the medical robot, with respect to the anatomy of interest of the patient.

PRESENTATION OF THE FIGURES

Figure 2:
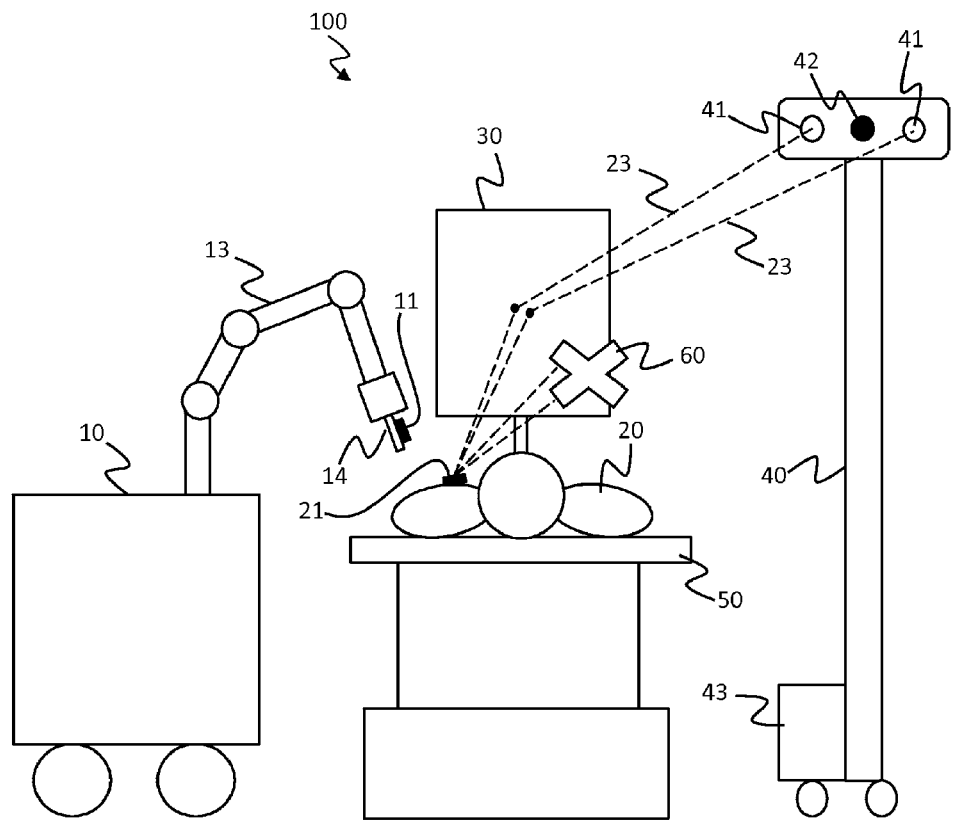
Figure 3:
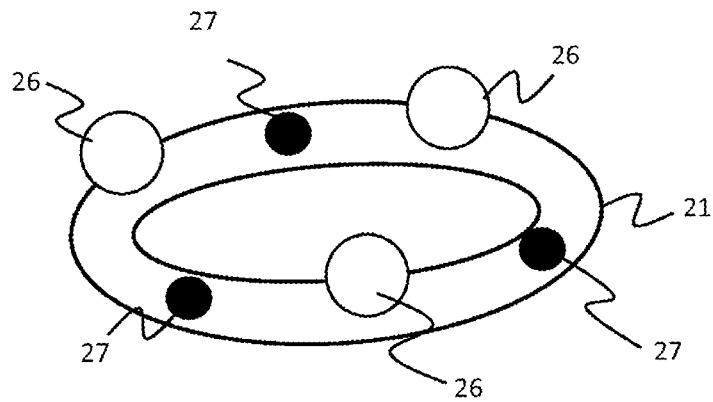
Figure 4:
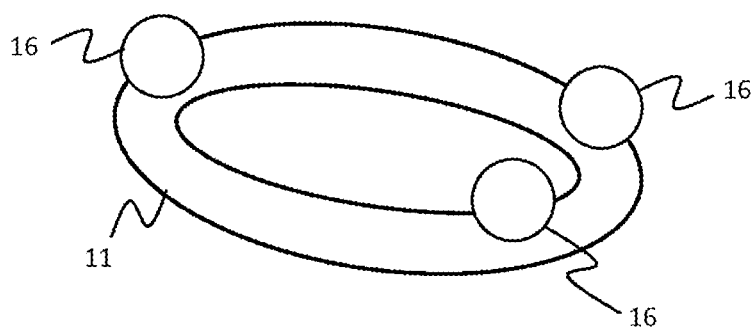
Figure 5:
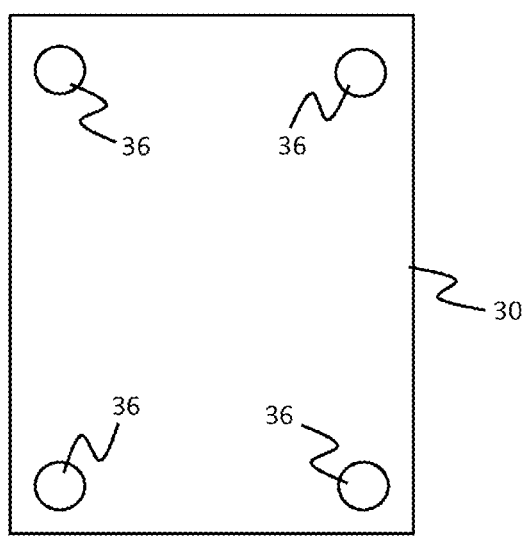
Figure 6:
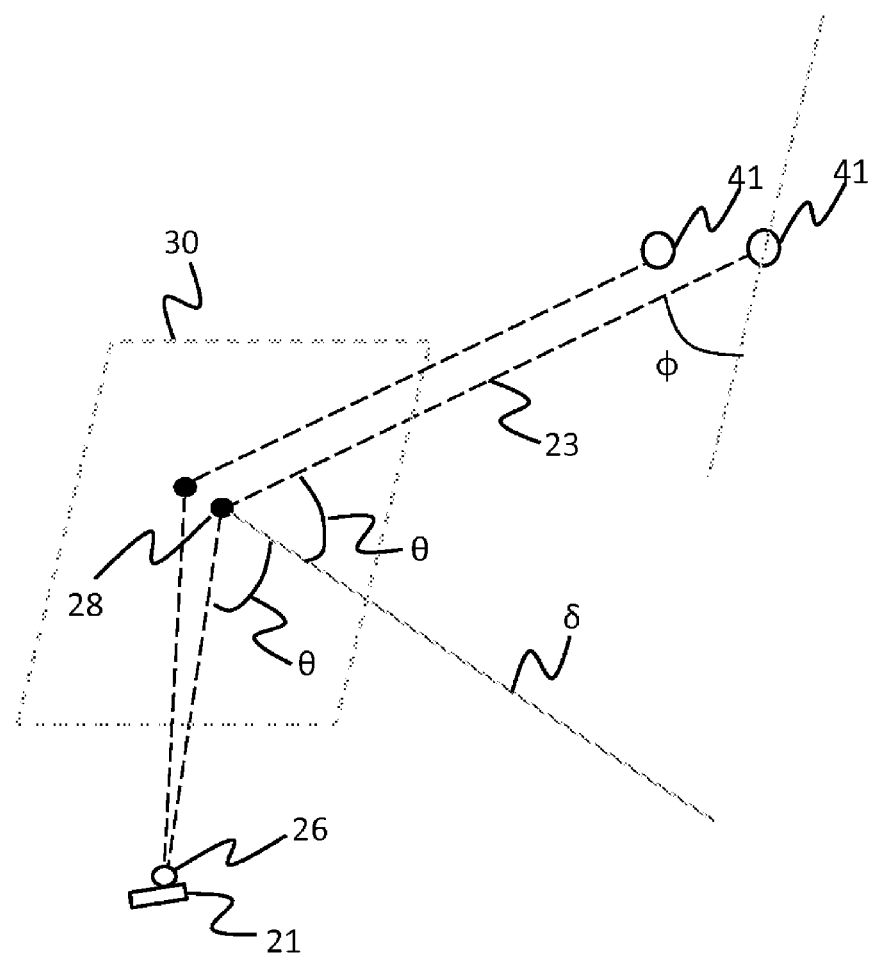
Figure 7:
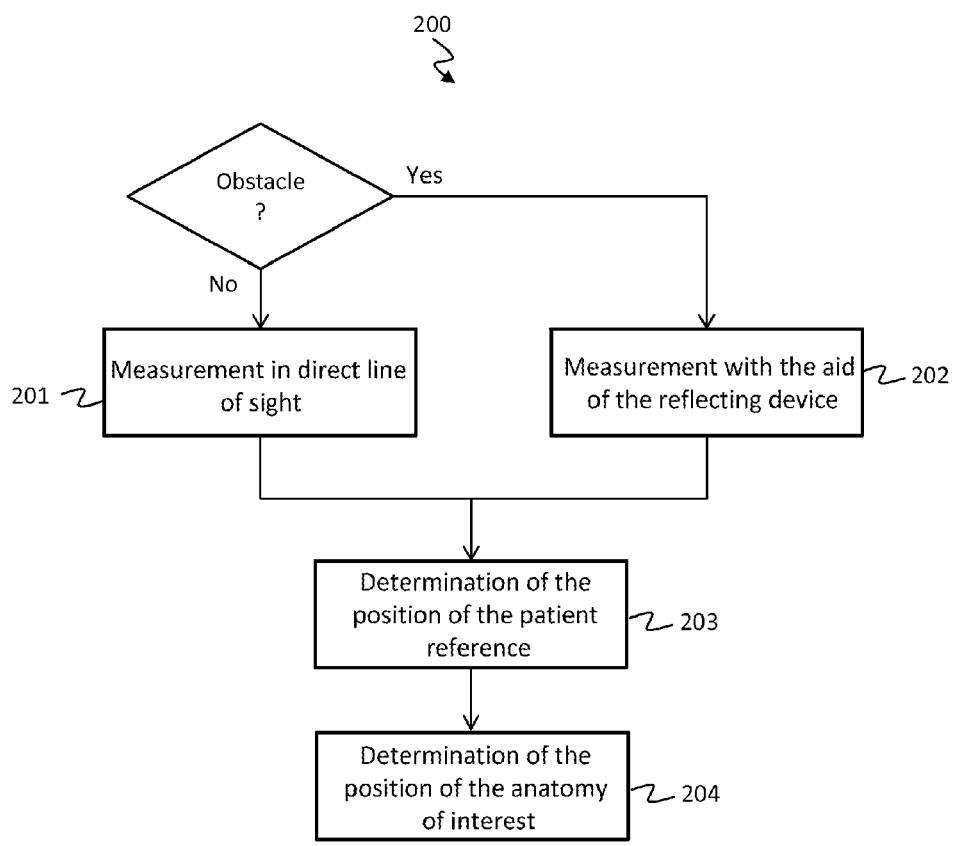
Figure 8:
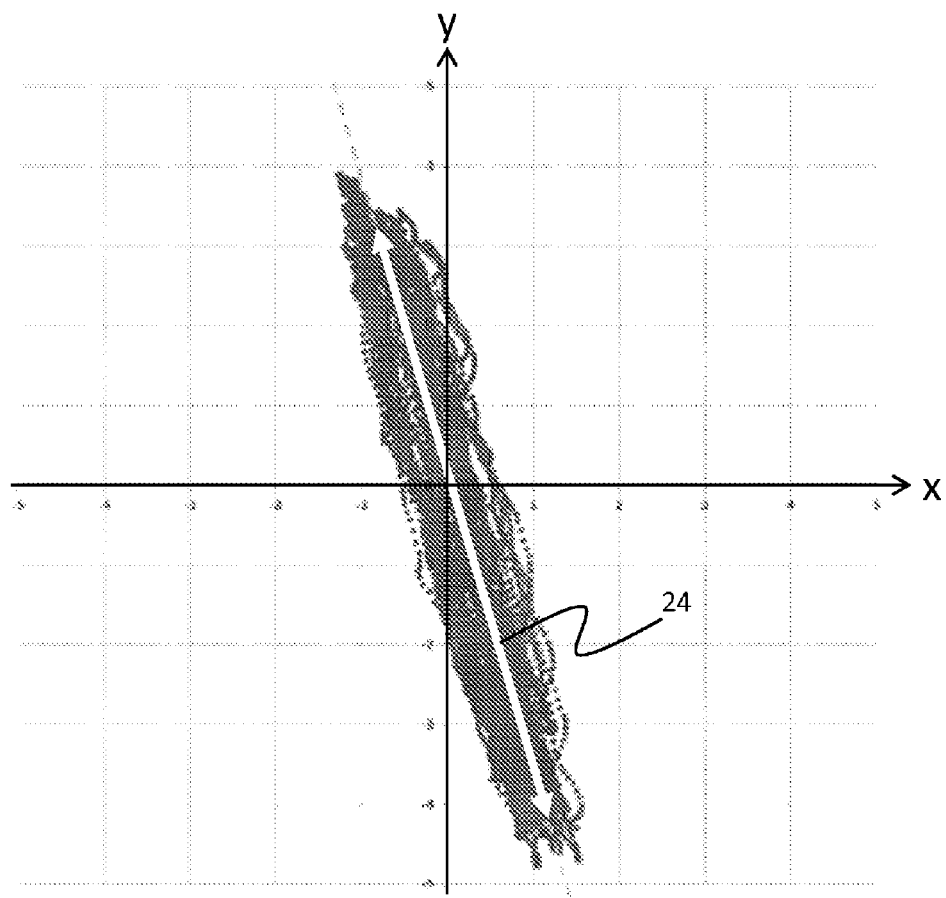
Figure 9A:
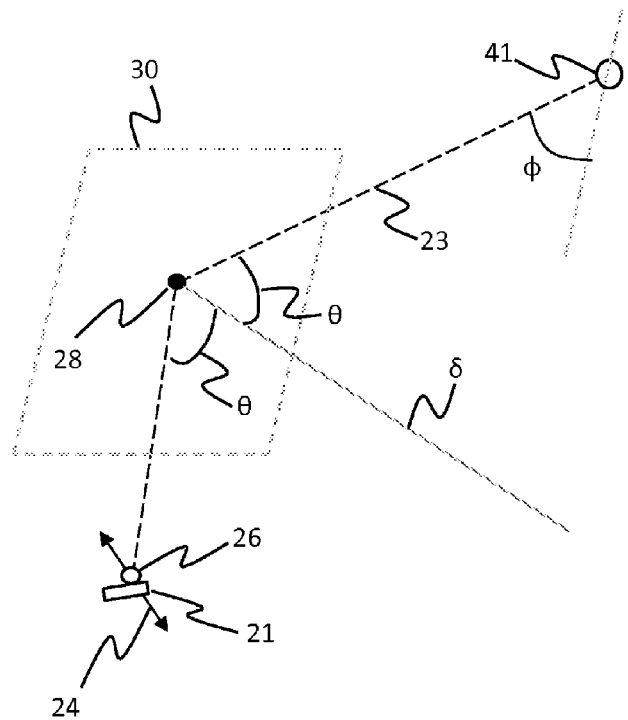
Figure 9B:
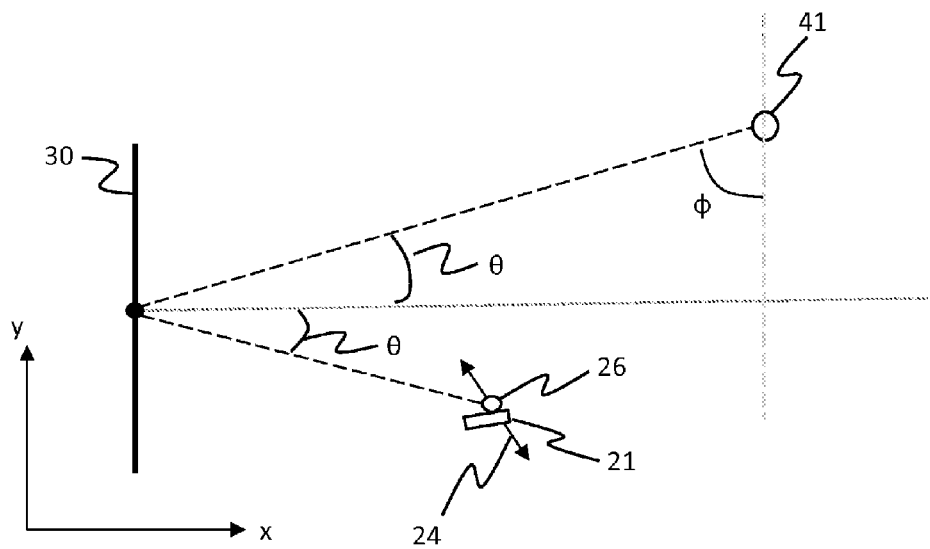
Figure 10:
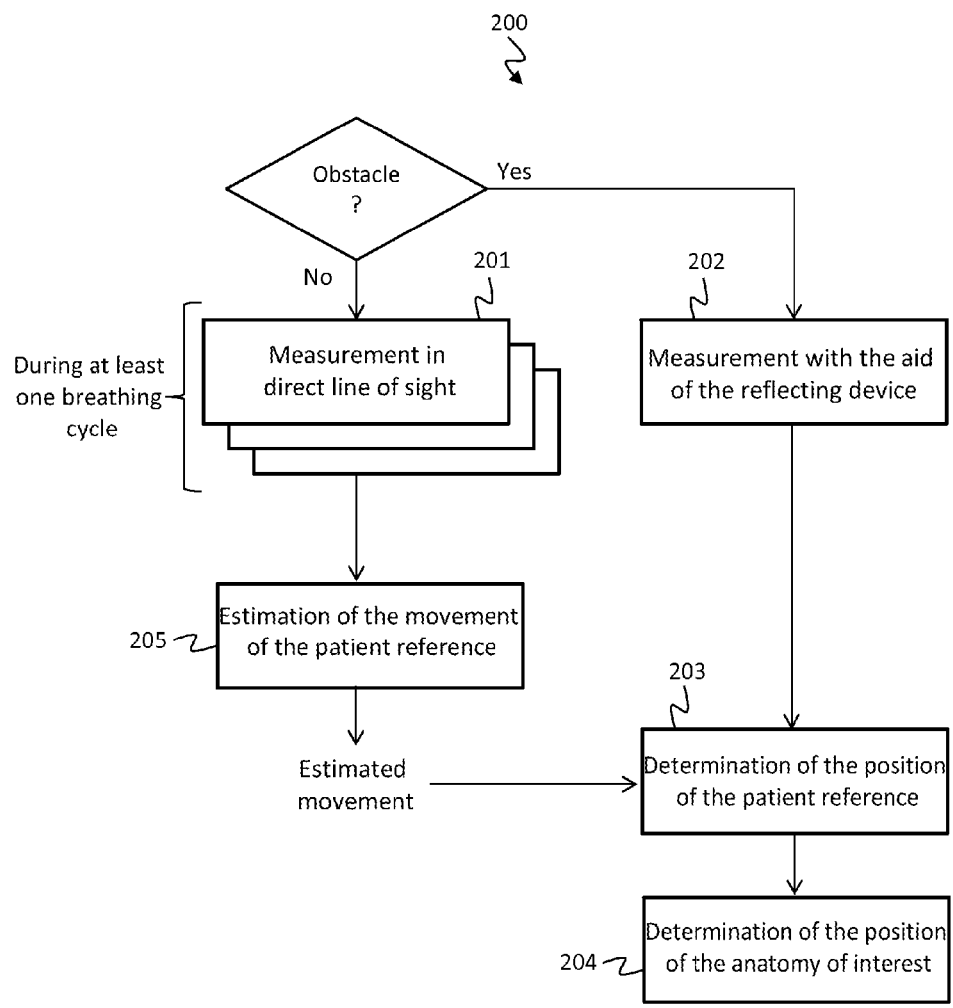

The invention will be better understood on reading the following description, given by way of non-limiting example, and made with reference to FIGS. 1 to 10, in which:

FIG. 1 is a schematic representation of an optical navigation system according to the invention when a direct line of sight is available, FIG. 2 is a schematic representation of an optical navigation system according to the invention when the line of sight is cut by an obstacle, FIG. 3 is a schematic representation of a patient reference having three optical markers and three radiopaque markers, FIG. 4 is a schematic representation of a robot reference having three optical markers, FIG. 5 is a schematic representation of a reflecting device having four optical markers, FIG. 6 is a schematic representation of the determination of the position of an optical marker of the patient reference, when the line of sight is cut by an obstacle, as a function of the measurements carried out by the optical sensors on optical rays reflected by the reflecting device, FIG. 7 is a schematic representation of the main steps of a method for determining the position of an anatomy of interest in a patient, FIG. 8 is a schematic representation of an estimated movement of the patient reference during a breathing cycle of the patient, FIG. 9a is a schematic representation of the determination of the position of an optical marker of the patient reference, when the line of sight is cut by an obstacle, as a function of the measurements carried out by the optical sensors and as a function of the estimated movement of the patient reference, FIG. 9b is a sectional view of FIG. 9a, FIG. 10 is a schematic representation of the main steps of a particular embodiment of a method for determining the position of an anatomy of interest in a patient.

In these figures, references that are identical from one figure to another designate identical or similar elements. For reasons of clarity, the elements shown are not necessarily on the same scale, unless otherwise indicated.

DETAILED DESCRIPTION OF AN EMBODIMENT OF THE INVENTION

FIG. 1 schematically shows an example of an optical navigation system 100 according to the invention.

In the example in question, illustrated in FIG. 1, the optical navigation system 100 has the following main elements: a locating device 40, a control unit 43, a patient reference 21 intended to be positioned at the anatomy of interest of a patient 20, and a reflecting device 30. In the example illustrated in FIG. 1, the patient 20 is lying on a table 50 in an operating room.

The object of the optical navigation system 100 is to determine the position of the patient reference 21 in order to deduce therefrom the position of the anatomy of interest in a frame of reference of the locating device 40. For this purpose, the control unit 43 is configured to implement all or some of the steps of a method making it possible to determine the position of the patient reference in the frame of reference of the locating device 40. The control unit 43 has, for example, one or more processors and a memory (magnetic hard disk, electronic memory, optical disk, etc.) in which a computer program product is stored in the form of a set of program code instructions to be executed in order to implement the different steps of such a method. Alternatively or in addition, the control unit 43 has one or more programmable logic circuits (FPGA, PLD, etc.) and/or one or more specialized integrated circuits (ASIC), and/or a set of discrete electronic components, etc., suitable for implementing all or some of the method steps.

As is illustrated in FIG. 1, the optical navigation system 100 can also include a robot reference intended to be positioned at a distal end of an articulated arm 13 of a medical robot 10, for example on an instrument holder 14 attached to said end. The control unit 43 can then be configured to determine also the position of the robot reference in the frame of reference of the locating device 40. If the position of a medical instrument, attached at the level of the instrument holder 14, with respect to the position of the robot reference 11 is known by the control unit 43, then the control unit 43 can determine the position of the medical instrument in the frame of reference of the locating device 40. The respective positions of the medical instrument and of the anatomy of interest relative to each other can then allow the medical robot 10 to configure its articulated arm such that the medical instrument is optimally positioned with respect to the anatomy of interest.

The control unit 43 can be integrated into the locating device 40, as is the case in the example illustrated in FIG. 1. The control unit 43 can also be a separate entity from the locating device 40 or else can be integrated into the medical robot 10. If the control unit 43 is not integrated into the medical robot 10, the control unit 43 can be configured to transmit, to the medical robot 10, information relating to the position of the anatomy of interest and/or the position of the medical instrument, such that the medical robot 10 can configure its articulated arm 13 so that the medical instrument is optimally positioned with respect to the anatomy of interest. This transmission of information can be effected, for example, via wireless communication means. If the control unit 43 is not integrated into the locating device 40, the control unit 43 is configured to receive, from the locating device 40, information relating to the position of the patient reference 21 and/or of the robot reference 11. The transmission of information between the locating device 40 and the control unit 43 can be effected, for example, via wireless communication means.

FIG. 3 shows schematically the patient reference 21. The patient reference 21 has at least three optical markers 26, such that the position of the patient reference 21 can be determined in the three spatial dimensions of the frame of reference of the locating device 40. The respective positions of the optical markers 26 of the patient reference 21 relative to each other are known a priori by the control unit 43. Advantageously, the geometric shape of each optical marker 26 can also be known a priori by the control unit 43. In the example illustrated in FIG. 3, the patient reference 21 has three optical markers 26 of spherical shape. The spherical shape makes it possible to optimize the reflection of the optical radiation.

The optical markers 26 can be passive or active. Passive optical markers reflect optical radiation emitted by another element, for example the locating device 40. Passive optical markers can correspond, for example, to reflecting spheres detectable by an infrared stereoscopic camera (this is what is used, for example, in the Polaris® navigation systems manufactured by the company Northern Digital Inc.), or to black and white patterns visible by a stereoscopic camera (this is what is used, for example, in the MicronTracker® navigation system from the company ClaroNav). Active optical markers themselves emit optical radiation, for example infrared radiation, detectable by the locating device 40.

FIG. 4 shows schematically the robot reference 11. The robot reference 11 has at least three optical markers 16, such that the position of the robot reference 11 can be determined in the three spatial dimensions of the frame of reference of the locating device 40. The respective positions of the optical markers 16 of the robot reference 11 relative to each other are known a priori by the control unit 43. Advantageously, the geometric shape of each optical marker 16 can also be known a priori by the control unit 43. In the example illustrated in FIG. 4, the robot reference 11 has three optical markers 16 of spherical shape. What has been mentioned above concerning the active or passive nature of the optical markers 26 of the patient reference 21 is also true for the optical markers 16 of the robot reference 11.

The respective positions of the optical markers 16 of the robot reference 11 relative to each other differ from the respective positions of the optical markers 26 of the patient reference 21 relative to each other. Such arrangements allow the locating device 40 to distinguish between the patient reference 21 and the robot reference 11.

As is illustrated in FIG. 1, the locating device 40 has at least two optical sensors 41 corresponding, for example, to two sensors of a stereoscopic camera operating in the infrared radiation field or in the visible light field. In the remainder of the description, it is considered by way of non-limiting example that the optical sensors 41 of the locating device 40 and the various optical markers 16, 21 of the optical navigation system 100 are designed to operate with optical radiation of the infrared type, that is to say electromagnetic radiation whose wavelength varies between 780 nm and 1 mm. However, it should be noted that the optical navigation system 100 according to the invention could also be designed to operate in the field of visible light (electromagnetic radiation whose wavelength varies between 380 nm and 780 nm) or in the field of ultraviolet radiation (electromagnetic radiation whose wavelength varies between 10 nm and 380 nm).

In a conventional manner, and as is illustrated in FIG. 1, when a direct line of sight is available between the patient reference 21 and the optical sensors 41 of the locating device 40 (that is to say when there is no obstacle between the patient reference 21 and the optical sensors 41 of the locating device 40, or in other words when the infrared radiation can follow a direct path 22 in a straight line between each optical marker 26 of the patient reference 21 and each optical sensor of the locating device 40), the position of each optical marker 26 can be determined as a function of the travel time of an infrared ray corresponding to said direct path 22 between said optical marker 26 and an optical sensor 41 (the speed of infrared radiation being known since it is equal to the speed of light), and/or as a function of an angle of arrival of said infrared ray at said optical sensor 41.

For example, when the optical markers 26 used in the optical navigation system 100 are passive markers, the optical sensors 41 can be configured to emit infrared radiation. This infrared radiation is then reflected by the various optical markers 26 toward the optical sensors 41. The optical sensors 41 are configured to receive this reflected infrared radiation. The distance between an optical marker 26 and an optical sensor 41 is then equal to half the time taken by an infrared ray to make the round trip between said optical sensor 41 and said optical marker 26 multiplied by the speed of light. By knowing the distance between each optical marker 26 and each optical sensor 41, and by knowing a priori the arrangement of the optical markers 26 with respect to each other on the patient reference 21, it is possible to determine the position of the patient reference 21 in the frame of reference of the locating device 40.

According to another example, when the optical markers 26 used in the optical navigation system 100 are active markers, each optical sensor 41 is configured to determine an angle of arrival, at said optical sensor 41, of the infrared radiation which is directly generated by an optical marker 26. By knowing for each optical marker 26 the angle of arrival at each optical sensor 41, and by knowing a priori the arrangement of the optical markers 26 with respect to each other on the patient reference 21, it is possible to determine the position of the patient reference 21 in the reference frame of the locating device 40.

Similarly, the locating device 40 can determine the position of the robot reference 11 in the frame of reference of the locating device 40 when a direct line of sight is available between the robot reference 11 and the optical sensors 41 of the locating device 40.

It should be possible to determine the position of the anatomy of interest of the patient from the position of the patient reference 21. For this purpose, and as is illustrated in FIG. 3, the patient reference 21 can have radiopaque markers 27. The respective positions of the radiopaque markers 27 relative to each other are known a priori by the control unit 43. Advantageously, the geometric shape of the radiopaque markers 27 can also be known a priori by the control unit 43. Preferably, the patient reference 21 has at least three radiopaque markers 27. The position of the anatomy of interest in the frame of reference of the locating device 40 can then be determined as a function of the position of the patient reference 21 in said frame of reference and as a function of a medical image of the anatomy of interest of the patient on which the radiopaque markers 27 of the patient reference 21 are visible. The medical image in fact gives information on the position of the anatomy of interest with respect to the position of the patient reference 21. By knowing the position of the patient reference 21 in the frame of reference of the locating device 40, it is then possible to deduce therefrom the position of the anatomy of interest in this frame of reference.

The radiopaque markers 27 can be, for example, ceramic balls or metal balls visible in a medical image (for example computed tomography, three-dimensional rotational angiography, magnetic resonance imaging, ultrasound, etc.). A medical image of the patient 20 is acquired with the patient reference 21. This medical image can be registered with another image of the same patient acquired previously and containing intervention planning data or can be used directly to plan the intervention. The planned intervention can be the ablation (for example by radiofrequency, microwaves, electroporation, laser, cryotherapy, ultrasound) of a tumor in an anatomy of interest (for example the liver, lungs or kidneys). The planned intervention can also be the insertion of a medical instrument into the brain, into the spinal column (for example for vertebroplasty and cementoplasty) or into another bone structure (for example the knee). Planning comprises determining the path to be followed by a medical instrument (for example a needle) between an entry point in the patient's skin and a target point (in the tumor) in the anatomy of the interest. Once the position of the anatomy of interest of the patient is determined in the frame of reference of the locating device, it is possible to deduce from these planning data the position that the medical instrument must take in this frame of reference.

As is illustrated in FIG. 2, a problem arises in determining the position of the patient reference 21 when an obstacle 60 cuts the line of sight between the patient reference 21 and the sensors 41 of the locating device 40 (and although this is not illustrated in FIG. 2, a similar problem arises in determining the position of the robot reference 11 when an obstacle intersects the line of sight between the robot reference 11 and the sensors 41 of the locating device).

To overcome this problem, the present invention proposes using a reflecting device 30 whose position in the frame of reference of the locating device 40 is known by the control unit 43.

The position of the reflecting device 30 is, for example, known a priori and stored in the memory of the control unit 43. In a variant, and as is illustrated in FIG. 5, the reflecting device 30 has at least three optical markers 36. The respective positions of the optical markers 36 relative to each other are known a priori by the control unit 43. Advantageously, the geometric shape of each optical marker 36 can also be known a priori by the control unit 43. The position of the reflecting device 30 can then be determined by the control unit 43 with the aid of the optical sensors 41 of the locating device 40. As is illustrated in FIGS. 1 and 2, the reflecting device 30 is, for example, fixed to the intervention table 50, and the position of the reflecting device 30 is not modified during the period of time when the anatomy of interest of the patient is to be determined.

The reflecting device 30 corresponds, for example, to a glass plate on which is glued a thin sheet of metal (for example of aluminum or silver), itself covered with a layer of copper or lead. Alternatively, the glass plate can be covered with a thin gold leaf. The reflecting device 30 can be a flat mirror or a concave mirror making it possible to concentrate the infrared rays. In the example in question, the reflecting device is a flat mirror of rectangular shape. As is illustrated in FIG. 5, an optical marker 36 can be positioned at each corner of the rectangle formed by the reflecting device 30.

As is illustrated in FIG. 2 and in FIG. 6, when a direct line of sight between the patient reference 21 and an optical sensor 41 is cut by an obstacle 60, the optical sensors 41 are configured to measure, for each optical marker 26 of the patient reference 21, a parameter representative of the position of said optical marker 26 in the frame of reference of the locating device 40, on the basis of an infrared ray coming from said optical marker 26 and following a path 23 reflected by the reflecting device 30 toward each optical sensor 41 (and not on the basis of an infrared ray corresponding to a direct path 22 between said optical marker 26 and said optical sensor 41). The expression "a parameter representative of the position of the marker" is understood to mean, for example, a travel time of the infrared ray between the optical sensor and the optical marker, or an angle of arrival of the infrared ray at the optical sensor 41.

For example, and as is illustrated in FIG. 6, if the angle of arrival of an infrared ray 23 reflected by the reflecting device 30 and coming from an optical marker 26 of the patient reference 21 is known for each optical sensor 41, and if the position of the reflecting device 30 is known, it is then possible to determine the position of said optical marker 26. It should be noted that the infrared ray 23 is reflected in the reflecting device 30 at a reflection point 28 by forming a reflection angle θ with respect to a straight line δ perpendicular to the reflecting device 30 and passing through the reflection point 28. This reflection angle θ is identical for the incident ray and for the reflected ray. In FIG. 6, the angle of arrival of the infrared ray 23 at the optical sensor 41 in a plane containing the infrared ray 23 and the straight line δ corresponds to the angle φ. If the angle of arrival φ at the optical sensor 41 and the position of the reflecting device 30 are known, it is possible to determine the value of the reflection angle θ. A reflection angle can thus be determined for the infrared ray associated respectively with each of the two optical sensors 41. The position of the optical marker 26 corresponds to the intersection of the two infrared rays.

It should be noted that the position of the optical marker 26 could also be determined from an optical sensor 41 as a function, on the one hand, of the angle of arrival of the infrared ray 23 and as a function, on the other hand, of the travel time of the infrared ray 23 between the optical marker 26 and the optical sensor 41 (on the assumption that this travel time can be determined).

FIG. 7 shows schematically the main steps of a method implemented by the control unit 43 in order to determine the position of the anatomy of interest of the patient.

The method 200 includes a first step in which it is detected whether an obstacle cuts a direct line of sight between the patient reference 21 and the optical sensors 41 of the locating device 40.

If a direct line of sight is available (no obstacle), the method 200 includes a step 201 in which measurements are carried out by the optical sensors 41 on the basis of infrared rays following direct paths 22 between the optical markers 26 of the patient reference 21 and the optical sensors 41.

If the line of sight is cut (presence of an obstacle), then the method 200 includes a step 202 in which measurements are carried out by the optical sensors 41 on the basis of infrared rays 23 following indirect paths, comprising a reflection on the reflecting device 30, between the optical markers 26 of the patient reference 21 and the optical sensors 41.

In step 203, the position of the patient reference 21 is determined from the positions of the optical markers 26 determined on the basis of the measurements carried out by the optical sensors 41.

In step 204, the position of the anatomy of interest 204 is determined from the position of the patient reference 21.

The optical sensors 41 are, for example, configured to work by default with infrared rays 23 coming directly from a work space in which the patient reference 21 and/or the robot reference 11 are assumed to be located. If such infrared rays are not detected, then the control unit 43 configures the optical sensors 41 such that the latter work on the basis of infrared rays 23 reflected by the reflecting device 30.

Thus, it is possible to determine the position of the anatomy of interest of the patient at any time, even when a direct line of sight is not available.

What has just been explained above concerning the determination of the position of the patient reference also applies to the determination of the robot reference 11 when an obstacle cuts the line of sight between the robot reference 11 and the sensors 41 of the locating device 40.

In particular embodiments, the medical robot 10 moreover has articulation encoders at the level of its articulated arm 13, making it possible to determine at any time the position of the robot reference 11 in a frame of reference of the medical robot 10. The medical robot 10 is configured to transmit, to the control unit 43, the position of the robot reference 11 in the frame of reference of the medical robot 10. The control unit 43 is configured to deduce therefrom the position of a medical instrument, attached to the distal end of the articulated arm 13 of the medical robot 10, with respect to the anatomy of interest of the patient 20.

For this purpose, it is for example conceivable, during a preliminary set-up step, that the articulated arm 13 of the medical robot 10 executes a predefined movement to make the robot reference 11 take up different calibration positions that are distributed in the common work space of the medical robot 10 and of the optical navigation system 100. For each calibration position taken up by the robot reference 11, the control unit 43 receives the position information on the one hand from the articulation encoders and on the other hand from the optical markers 16 of the robot reference 11. The frame of reference of the medical robot 10 and the frame of reference of the locating device 40 can be readjusted (registered) by matching the different calibration positions and calculating the rigid registration point by point.

As the patient breathes, the anatomy of interest of the patient (and more particularly a target zone within the anatomy of interest) follows the breathing movements. It should be possible to follow the position of the anatomy of interest over the course of time with the aid of the optical navigation system 100, even during periods when the line of sight between a marker, positioned at the anatomy of interest, and an optical sensor of the navigation system is cut by an obstacle.

FIG. 8 shows schematically the movement of the patient reference 21 over a period of time comprising several breathing cycles of the patient. The movement is shown in a system with two coordinates x and y. Each axis x or y thus corresponds to a component of the movement of the patient reference 21.

For example, during the time period in question, a direct line of sight is always available between the patient reference 21 and the optical sensors 41 of the locating device 40. The position of each optical marker 26 of the patient reference 21 is determined at several instants during the time period. It is then possible to determine, for the time period in question, an estimated movement 24 corresponding, for example, to the average movement of the patient reference 21, on the two components chosen, during a breathing cycle of the patient. In the remainder of the description, it is considered for simplicity that the estimated movement 24 of the patient reference 21 is substantially identical to the movement followed by each optical marker 26 of the patient reference 21. In reality, each optical marker 26 of the patient reference 21 could have a particular movement, and the movement of the patient reference would then correspond to a resultant of the movements of the various optical sensors (it would then be conceivable to consider an estimated movement for each optical marker 26 of the patient reference 21).

FIGS. 9*a* and 9*b* show schematically how the position of an optical marker 26 of the patient reference can be determined as a function of the estimated movement 24 of said optical marker 26 when the line of sight is cut by an obstacle. FIG. 9*b* is a two-dimensional representation of FIG. 9*a* in the plane containing the infrared ray 23, coming from the optical marker 26 and reflected by the reflecting device 30, and also the straight line δ perpendicular to the reflecting device 30 and passing through the reflection point 28.

As is illustrated in FIGS. 9*a* and 9*b*, when the line of sight is no longer available between the patient reference 21 and an optical sensor 41, it is possible to determine the position of an optical marker 26 as a function, on the one hand, of the measurements carried out by an optical sensor 41 on the basis of the optical ray 23 coming from said optical marker 26 of the patient reference 21 and reflected by the reflecting device 30, and as a function, on the other hand, of the estimated movement 24 of the optical marker 26. As is illustrated in FIG. 9*b*, the estimated movement 24 of the optical marker 26 is broken down into two orthogonal components x and y belonging to the plane containing the infrared ray 23 and the straight line δ. The infrared ray 23 is reflected in the reflecting device 30 at the reflection point 28, forming a reflection angle θ with respect to the straight line δ. This reflection angle θ is identical for the incident ray and for the reflected ray. The infrared ray 23 forms an angle of arrival φ at the optical sensor 41.

If the angle of arrival φ at the optical sensor 41 and the position of the reflecting device 30 are known, it is possible to determine the value of the reflection angle θ. It is then possible to determine the position of the optical marker 26, because it corresponds to the intersection of the infrared ray 23 with the path followed by the estimated movement 24 of the optical marker 26.

According to another example, if the travel time of the infrared ray 23 between the optical marker 26 and the optical sensor 41 is known, in other words if the distance traveled by said infrared ray is known, it is also possible to determine the position of the optical marker 26, because there is only a single point on the path followed by the estimated movement 24 of the optical marker 26 from which an infrared ray 23 reflecting on the reflecting device 30 would reach the optical sensor 41 by traveling said distance.

Once the position of each optical marker 26 is determined, the position of the patient reference 21 can also be determined. It is then possible to deduce therefrom the position of the anatomy of interest, especially if the position of the anatomy of interest can be defined with respect to the position of the patient reference on a medical image.

It is moreover possible to use a biomechanical model of the anatomy of interest in order to optimize the determination of the position of the anatomy of interest as a function of the position of the patient reference 21 and the estimated movement 24 followed by the patient reference 21. It is indeed possible to model, in the form of a biomechanical model, the deformations of the various anatomical structures (muscles, tendons, bone structures, organs, vascular network, etc.) and the mechanical interactions between these various structures. The biomechanical model can then make it possible to better define the movement followed by the anatomy of interest as a function of the movement followed by the patient reference 21.

FIG. 10 schematically shows a particular embodiment of the method 200 described with reference to FIG. 7. In particular, the step 201 of measuring, in direct line of sight, the position of the optical markers of the patient reference is repeated at several different instants during a time period comprising at least one breathing cycle of the patient. As has been previously described with reference to FIG. 8, this makes it possible, at step 205, to estimate a movement of the patient reference 21 during a breathing cycle of the patient. This estimated movement 24 is then used at step 203 to determine the position of the patient reference 21 when the line of sight is no longer available (as has been previously described with reference to FIGS. 9*a* and 9*b*). The position of the anatomy of interest of the patient can then be determined, at step 204, from the position of patient reference 21.

The invention thus makes it possible to determine the position of an anatomy of interest of a patient with the aid of an optical navigation system 100 even when a direct line of sight is not available between the patient reference 21 and the optical sensors 41 of a locating device 40 of the optical navigation system 100.

In particular embodiments, and as is illustrated in FIGS. 1 and 2, the locating device 40 can moreover have a camera 42 which supplies images to the control unit 43 in order to determine an insertion depth of the medical instrument during the intervention. Images of the intervention are taken continuously by the camera 42. When the medical robot 10 is positioned with respect to the patient in accordance with the intervention plan, the practitioner inserts the medical instrument (for example a needle) into the anatomy of interest of the patient in order to reach a target zone (for example a tumor). The images from the camera 42 are analyzed by the control unit 43, which is configured to detect the medical instrument. Knowing the total length of the medical instrument and the position of the target zone to be reached, the control unit 43 can determine the insertion depth of the medical instrument and determine when the instrument has reached the target zone. When the target zone is reached, a message for the attention of the practitioner is displayed for example on a control screen. The message can be accompanied by an acoustic signal.

In particular embodiments, the images provided by the camera 42 of the locating device 40 are analyzed by the control unit 43 in order to recognize gestures made by a hand (gloved or not) of the practitioner, said gestures being associated with particular commands intended for the medical robot 10 (for example for configuring the articulated arm of the medical robot in a predetermined position, for moving the base of the medical robot to a predetermined position, for urgently interrupting any movement of the medical robot, etc.). The gestures made by the practitioner may obstruct the line of sight between the patient reference 21 and the optical sensors 41, but the reflecting device 30 nonetheless allows the optical navigation system 100 according to the invention to determine the position of the patient reference 21.

It should be noted that several reflecting devices 30 can be used in order to increase the number of different paths followed by optical radiation coming from an optical marker. In particular embodiments, the optical navigation system 100 advantageously has three different reflecting devices arranged orthogonally in pairs. When a direct line of sight is not available, the position of the patient reference 21 can then be determined from optical rays reflected by one or more of the reflecting devices.

The invention claimed is:

1. An optical navigation system for determining the position of an anatomy of interest of a patient, comprising:
   a locating device comprising at least two optical sensors,
   a control unit,
   a patient reference comprising at least three optical markers, the respective positions of the optical markers relative to each other being known a priori by the control unit, said patient reference being intended to be positioned on the patient at the anatomy of interest, a reflecting device whose position in a frame of reference of the locating device can be determined by the control unit, wherein when a direct line of sight between the patient reference and each optical sensor is available, the optical sensors are configured to measure, for each optical marker of the patient reference, a parameter representative of the position of said optical marker in the frame of reference of the locating device, on the basis of optical radiation coming from said optical marker and having for each optical sensor a direct path between said optical marker and said optical sensor, wherein when a direct line of sight between the patient reference and an optical sensor is cut by an obstacle, the optical sensors are configured to measure, for each optical marker of the patient reference, a parameter representative of the position of said optical marker in the frame of reference of the locating device, on the basis of optical radiation coming from said optical marker and having a path reflected by the reflecting device toward each optical sensor, and wherein the control unit is configured to determine, from the measurements carried out by the optical sensors, the position of the patient reference in the frame of reference of the locating device, and to deduce therefrom the position of the anatomy of interest in said frame of reference.

2. The optical navigation system of claim 1, wherein the reflecting device comprises at least three optical markers, the respective positions of the optical markers relative to each other being known a priori by the control unit.

3. The optical navigation system of claim 1, wherein the control unit is configured:

to estimate, during a period when a direct line of sight between the patient reference and each optical sensor is available, a movement followed by the patient reference in the frame of reference of the locating device during a breathing cycle of the patient, and to determine, at a time when a direct line of sight between the patient reference and an optical sensor is no longer available, the position of the patient reference as a function, on the one hand, of the measurements carried out by the optical sensors on the basis of the optical radiation coming from the optical markers of the patient reference and reflected by the reflecting device, and as a function, on the other hand, of the estimated movement of the patient reference.

4. The optical navigation system of claim 1, wherein the patient reference further comprises at least three radiopaque markers, the respective positions of the radiopaque markers relative to each other being known a priori by the control unit.

5. The optical navigation system of claim 4, wherein the position of the anatomy of interest in the frame of reference of the locating device is determined as a function of the position of the patient reference in said frame of reference, and as a function of a medical image of the anatomy of interest of the patient on which the radiopaque markers of the patient reference are visible.

6. The optical navigation system of claim 5, in which the position of the anatomy of interest in the frame of reference of the locating device is further determined as a function of a biomechanical model of the anatomy of interest.

7. The optical navigation system of claim 1, wherein the optical navigation system comprises three reflecting devices orthogonal in pairs.

8. The optical navigation system of claim 1, further comprising a robot reference intended to be positioned at a distal end of an articulated arm of a medical robot, said robot reference having at least three optical markers, the respective positions of the optical markers relative to each other being known a priori by the control unit, wherein when a direct line of sight between the robot reference and each optical sensor is available, the optical sensors are configured to measure, for each optical marker of the robot reference, a parameter representative of the position of said optical marker in the frame of reference of the locating device, on the basis of optical radiation coming from said optical marker and having for each optical sensor a direct path between said optical marker and said optical sensor, wherein when a direct line of sight between the robot reference and an optical sensor is cut by an obstacle, the optical sensors are configured to measure, for each optical marker of the robot reference, a parameter representative of the position of said optical marker in the frame of reference of the locating device, on the basis of optical radiation coming from said optical marker and having a path reflected by the reflecting device toward each optical sensor, and wherein the control unit is configured to determine the position of the robot reference in the frame of reference of the locating device on the basis of the measurements thus carried out by the optical sensors.

9. The optical navigation system of claim 8, wherein the optical markers of the patient reference and/or of the robot reference are active markers, and the optical radiation coming from an optical marker is infrared radiation generated by said optical marker.

10. The optical navigation system of claim 8, wherein the optical markers of the patient reference and/or of the robot reference are passive markers, and the optical radiation coming from an optical marker is infrared radiation generated by the locating device and reflected by said optical marker.

11. The optical navigation system of claim 1, further comprising a medical robot having comprising an articulated arm, the robot reference being positioned at a distal end of the articulated arm, said medical robot further comprising articulation encoders of the articulated arm, making it possible to determine at any time the position of the robot reference in a frame of reference of the medical robot, the medical robot being configured to transmit to the control unit the position of the robot reference in the frame of reference of the medical robot, and the control unit is configured to deduce therefrom the position of a medical instrument, attached to the distal end of the articulated arm of the medical robot, with respect to the anatomy of interest of the patient.

12. The optical navigation system of claim 11, wherein the optical markers of the patient reference and/or of the robot reference are active markers, and the optical radiation coming from an optical marker is infrared radiation generated by said optical marker.

13. The optical navigation system of claim 11, wherein the optical markers of the patient reference and/or of the robot reference are passive markers, and the optical radiation coming from an optical marker is infrared radiation generated by the locating device and reflected by said optical marker.

14. A method for determining the position of an anatomy of interest of a patient, said method being implemented by an optical navigation system comprising:

- a locating device comprising at least two optical sensors,
- a patient reference comprising at least three optical markers, the respective positions of the optical markers relative to each other being known a priori, said patient reference being intended to be positioned on the patient at the anatomy of interest, wherein the optical navigation system further comprises a reflecting device whose position in a frame of reference of the locating device is known, and the method has the following steps:

- when a direct line of sight between the patient reference and each optical sensor is available, measuring, for each optical marker of the patient reference, of a parameter representative of the position of said optical marker in the frame of reference of the locating device, on the basis of optical radiation coming from said optical marker and having for each optical sensor a direct path between said optical marker and said optical sensor,
- when a direct line of sight between the patient reference and an optical sensor is cut by an obstacle, measuring, for each optical marker of the patient reference, of a parameter representative of the position of said optical marker in the frame of reference of the locating device, on the basis of optical radiation coming from said optical marker and having a path reflected by the reflecting device toward each optical sensor,
- determining, on the basis of the measurements thus carried out by the optical sensors, of the position of the patient reference in the frame of reference of the locating device, and
- determining, in said frame of reference of the locating device, the position of the anatomy of interest on the basis of the position of the patient reference.

15. The method of claim 14, further comprising the following steps:

- during a period when a direct line of sight between the patient reference and each optical sensor is available, estimating a movement followed by the patient reference in the frame of reference of the locating device during a breathing cycle of the patient, and
- at a time when a direct line of sight between the patient reference and an optical sensor is no longer available, determining the position of the patient reference as a function, on the one hand, of the measurements carried out by the optical sensors on the basis of the optical radiation coming from the optical markers of the patient reference and reflected by the reflecting device, and as a function, on the other hand, of the estimated movement of the patient reference.

16. The method of claim 15, wherein the position of the anatomy of interest in the frame of reference of the locating device is further determined on the basis of a medical image of the anatomy of interest of the patient on which radiopaque markers of the patient reference are visible.

17. The method of claim 16, wherein the position of the anatomy of interest in the frame of reference of the locating device is further determined on the basis of a biomechanical model of the anatomy of interest.

18. The method of claim 14, wherein the optical navigation system further comprises a robot reference intended to be positioned at a distal end of an articulated arm of a medical robot, said robot reference comprising at least three optical markers, the respective positions of the optical markers relative to each other being known a priori, said method comprising the following steps:

- when a direct line of sight between the robot reference and each optical sensor is available, measuring, for each optical marker of the robot reference, a parameter representative of the position of said optical marker in the frame of reference of the locating device, on the basis of optical radiation coming from said optical marker and having for each optical sensor a direct path between said optical marker and said optical sensor,
- when a direct line of sight between the robot reference and an optical sensor is cut by an obstacle, measuring, for each optical marker of the robot reference, of a parameter representative of the position of said optical marker in the frame of reference of the locating device, on the basis of optical radiation coming from said optical marker and having a path reflected by the reflecting device toward each optical sensor, and
- determining the position of the robot reference in the frame of reference of the locating device, on the basis of the measurements thus carried out by the optical sensors.

19. The method of claim 18, wherein the optical navigation system further comprises a medical robot comprising an articulated arm, the robot reference being positioned at a distal end of the articulated arm, said medical robot further comprising articulation encoders of the articulated arm, making it possible to determine at any time the position of the robot reference in a frame of reference of the medical robot, said method further comprising a step of determining the position of a medical instrument, attached to the distal end of the articulated arm of the medical robot, with respect to the anatomy of interest of the patient.

* * * * *